(12) United States Patent
Fujisawa (10) Patent No.: US 7,260,252 B2
(45) Date of Patent: Aug. 21, 2007

(54) X-RAY COMPUTED TOMOGRAPHIC APPARATUS, IMAGE PROCESSING APPARATUS, AND IMAGE PROCESSING METHOD

(75) Inventor: Yasuko Fujisawa, Otawara (JP)

(73) Assignee: Kabushiki Kaisha Toshiba, Tokyo (JP)

( * ) Notice: Subject to any disclaimer, the term of this patent is extended or adjusted under 35 U.S.C. 154(b) by 785 days.

(21) Appl. No.: 10/685,489

(22) Filed: Oct. 16, 2003

(65) Prior Publication Data

US 2004/0087853 A1 May 6, 2004

(30) Foreign Application Priority Data

Oct. 22, 2002 (JP) ............................. 2002-307168

(51) Int. Cl.
*G06K 9/00* (2006.01)

(52) U.S. Cl. ...................... 382/131; 382/285; 600/425

(58) Field of Classification Search ................ 600/425; 382/132, 131
See application file for complete search history.

(56) References Cited

U.S. PATENT DOCUMENTS

| 5,800,355 | A  | * | 9/1998  | Hasegawa ............... 600/436 |
| 5,970,182 | A  | * | 10/1999 | Goris ...................... 382/278 |
| 5,971,767 | A  | * | 10/1999 | Kaufman et al. ......... 434/267 |
| 6,628,743 | B1 | * | 9/2003  | Drummond et al. ......... 378/8 |
| 7,194,117 | B2 | * | 3/2007  | Kaufman et al. ......... 382/128 |
| 2001/0031920 | A1 | * | 10/2001 | Kaufman et al. ......... 600/431 |
| 2005/0031179 | A1 | * | 2/2005  | Wehrli et al. ............. 382/131 |

FOREIGN PATENT DOCUMENTS

| JP | 60-218166 | | 10/1985 |
| JP | 63-044103 | | 2/1988 |
| JP | 05-045117 A | * | 8/1991 |
| JP | 5-045117 | | 2/1993 |
| JP | 6-147830 | | 5/1994 |
| JP | 6-229720 | | 8/1994 |
| JP | 2562047 | | 9/1996 |

OTHER PUBLICATIONS

Let's Play PET, last updates Sep. 14, 2000, "http://www.crump.ucla.edu/software/lpp/lpphome.html", section 5. Clinical Application of PET ; Polar Maps, Dept. of Molecular and Medical Pharmacology ; UCLA School of Medicine , Johannes Czernin, M.D.; Sanjiv Gambhir, M.D., Ph.D.Richard Brunken; M.D.; Heinrich R. Schelbert, M.D., Ph.D.*
Notification of Grounds for Rejection dated Oct. 28, 2004.

* cited by examiner

*Primary Examiner*—Joseph Mancuso
*Assistant Examiner*—Nancy Bitar
(74) *Attorney, Agent, or Firm*—Oblon, Spivak, McClelland, Maier & Neustadt, P.C.

(57) ABSTRACT

An image processing apparatus includes an index computing unit that computes motion functional indices of a particular organ from volume data of a subject including the particular organ, a polar map generating unit that generates a polar map by developing the indices on a polar coordinate system, an image generating unit that generates, from the volume data, an image related to a structure of one of the particular organ and a peripheral organ developed on the polar coordinate system, a fusing unit that fuses the image into the polar map, and a display unit that displays a polar map fused with the image.

20 Claims, 13 Drawing Sheets

X-RAY COMPUTED TOMOGRAPHIC APPARATUS, IMAGE PROCESSING APPARATUS, AND IMAGE PROCESSING METHOD

CROSS-REFERENCE TO RELATED APPLICATIONS

This application is based upon and claims the benefit of priority from the prior Japanese Patent Application No. 2002-307168, filed Oct. 22, 2002, the entire contents of which are incorporated herein by reference.

BACKGROUND OF THE INVENTION

1. Field of the Invention

The present invention relates to an X-ray computed tomographic apparatus, an image processing apparatus, and an image processing method used to generate a polar map related to functional indices about organs, such as a heart.

2. Description of the Related Art

Speedups in helical scan and developments in volume scan using a 2-D detector have greatly changed the concept of an X-ray computed tomographic apparatus from a mere cross-section imaging apparatus to a volume imaging apparatus. In other words, an X-ray computed tomographic apparatus adopting these scan methods has enabled fast scan of a subject in volume at a short temporal resolution. Practical applications of an X-ray computed tomographic apparatus equipped with these functions have found a way into many diagnostic fields where the X-ray computed tomographic apparatus has not been used, and an effort to find a novel diagnostic method is being made.

One of the possible directions is adaptation to evaluation diagnosis on palmic motions of the heart. Together with the segment scan method, the volume scan substantially achieves successive scanning of the entire heart in short cycles. This makes it possible to generate, for example, a stereoscopic image of the heart limited in the end of diastole (ED) or the end of systole (ES). Further, it is possible to find cardiac functional indices, such as wall thickening from ED to ES, across the entire heart. The heart extends longitudinally from the apex to the base, and a polar map is used to enable observation of a distribution of the cardiac functional indices across the longitudinal heart at a glance. As is known, a polar map is an expression method of a plane by developing data on polar coordinates expressed as (r, θ). In the case of the heart, θ is given as an angle about the myocardial axis, and r is given as a distance to each slice in a direction from the apex to the base of the heart.

Figure 20:
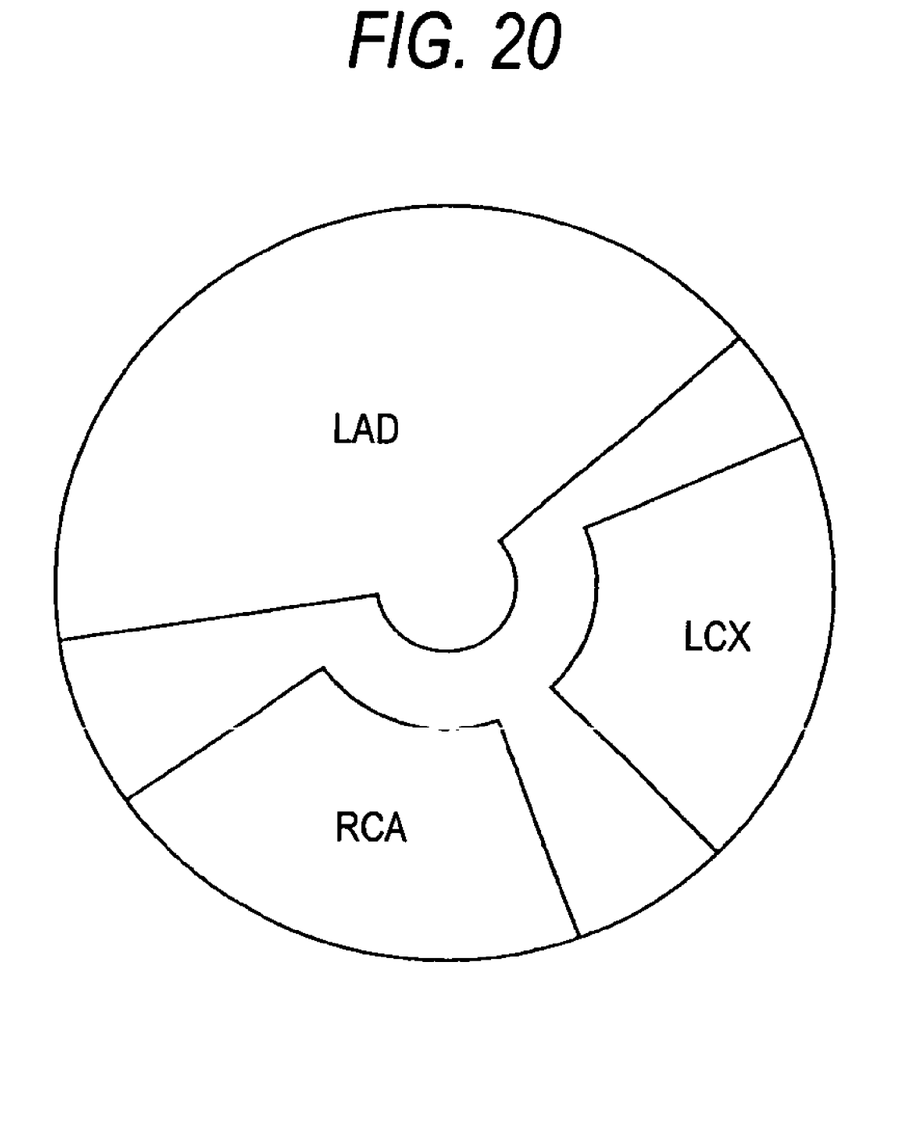
FIG. 20 is a view showing dominant regional segments superimposed on a polar map in related arts.

A polar map makes it easy to observe a portion causing deterioration in the cardiac function, for example, by a difference in display colors. When used in a diagnosis actually, a relation between the deteriorated portion and a dominant blood vessel is needed. Hence, as shown in FIG. 20, a polar map, when displayed, is often superimposed with anatomically divided, established typical dominant regional segments. A segment denoted by "LAD" represents a dominant region of the left anterior descending branch, a segment denoted by "LCX" represents a dominant region of the left circumflex branch, and a segment denoted by "RCA" represents a dominant region of the right coronary artery.

By displaying a polar map superimposed with the typical dominant regional segments as has been described, it is possible to understand in which of the left anterior descending branch, the left circumflex branch, and the right coronary artery a lesion is caused in a coronary artery, that is, in which dominant region of an artery a lesion is caused; however, place and location of a lesion in the coronary artery cannot be specified.

BRIEF SUMMARY OF THE INVENTION

It is therefore an object of the invention to improve the diagnostic capability of a polar map related to the function of an organ.

According to an aspect of the invention, there is provided an image processing apparatus, including: an index computing unit configured to compute motion functional indices of a particular organ from volume data of a subject including the particular organ; a polar map generating unit configured to generate a polar map by developing the indices on a polar coordinate system; an image generating unit configured to generate, from the volume data, an image related to a structure of one of the particular organ and a peripheral organ developed on the polar coordinate system; a fusing unit configured to fuse the image into the polar map; and a display unit configured to display a polar map fused with the image.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate presently preferred embodiments of the invention, and together with the general description given above and the detailed description of the preferred embodiments given below, serve to explain the principles of the invention.

DETAILED DESCRIPTION OF THE INVENTION

Embodiments of an X-ray computed tomographic apparatus (X-ray CT scanner), an image processing apparatus, and an image processing method of the invention will now be described with reference to the drawings. An explanation will be given to an X-ray CT scanner in this embodiment. The X-ray CT scanner described below, however, is equipped with an image processing apparatus furnished with a function of achieving an image processing method of this embodiment.

Incidentally, an X-ray CT scanner includes various types, such as a ROTATE/ROTATE type in which an X-ray tube and a radiation detector integrally rotate about a subject, and a STATIONARY/ROTATE type in which a number of detecting elements are aligned in a ring-shaped array and an X-ray tube alone rotates about a subject, and the invention is applicable to any type. Herein, an explanation will be given to a popular ROTATE/ROTATE type. Also, projection data of a full circle, that is, approximately 360° about a subject is needed to reconstruct tomographic data of one slice, and projection data of 180° plus a view angle is needed in the half-scan method. The invention is applicable to either reconstruction method. Herein, an explanation will be given to the half-scan method by way of example. In addition, as a mechanism by which an incident X-ray is converted to electric charges, an indirect converting method and a direct converting method are popular: in the former indirect converting method, an X-ray is converted into light by a fluorescent substance, such as a scintillator, and the light is further converted into electric charges by a photo-electric converting element, such as a photo-diode; and in the latter direct converting method, generation of electron-hole pairs inside a semiconductor by an X-ray and movements of these electrons and holes toward the electrodes, that is, a photo-conductive phenomenon are used. An X-ray detecting element may adopt either method, and herein, an explanation will be given to the former indirect converting method. Further, a so-called multi-tube X-ray CT scanner having more than one pair of an X-ray tube and an X-ray detector in a rotational ring has been becoming commercially available in recent years, and peripheral techniques have been developed accordingly. The invention is applicable to either a convention single-tube X-ray CT scanner or a multi-tube X-ray CT scanner. Herein, an explanation will be given to a single-tube type.

In this embodiment, indices related to a motion function of a particular organ are computed from multi-slice data or volume data of a subject including the particular organ. The functional indices thus computed are developed on the polar coordinate system, so that a polar map (initial polar map) related to the organ function is generated. Also, the morphology of the particular organ or a peripheral organ is developed on the polar coordinate system from the same volume data, so that an image (data set) related to the morphology is generated. The morphological data is then fused into the polar map, and a polar map fused with the morphological data is thereby displayed.

The volume data is generated, in general, by an X-ray computed tomographic apparatus. In the invention, however, volume data is not limited to the volume data generated by an X-ray computed tomographic apparatus, and volume data generated by an X-ray diagnostic apparatus, a SPECT apparatus, a PET apparatus, an MRI apparatus, or an ultrasonic diagnostic apparatus can be handled as well.

This embodiment is most effective in a case where a polar map is generated by specifying the heart, in particular, a myocardium in the left ventricle, as the particular organ, and an image of a coronary artery structure developed on the polar coordinate system is fused into the polar map. Hereinafter, an explanation will be given to an example of the most effective case where a polar map related to a myocardium in the left ventricle is generated, and an image of a coronary artery structure developed on the polar coordinate system is fused into the polar map. It should be appreciated, however, that the particular organ is limited neither to the heart nor a myocardium in the left ventricle, and the peripheral organ is not limited to a coronary artery, either.

Figure 1:
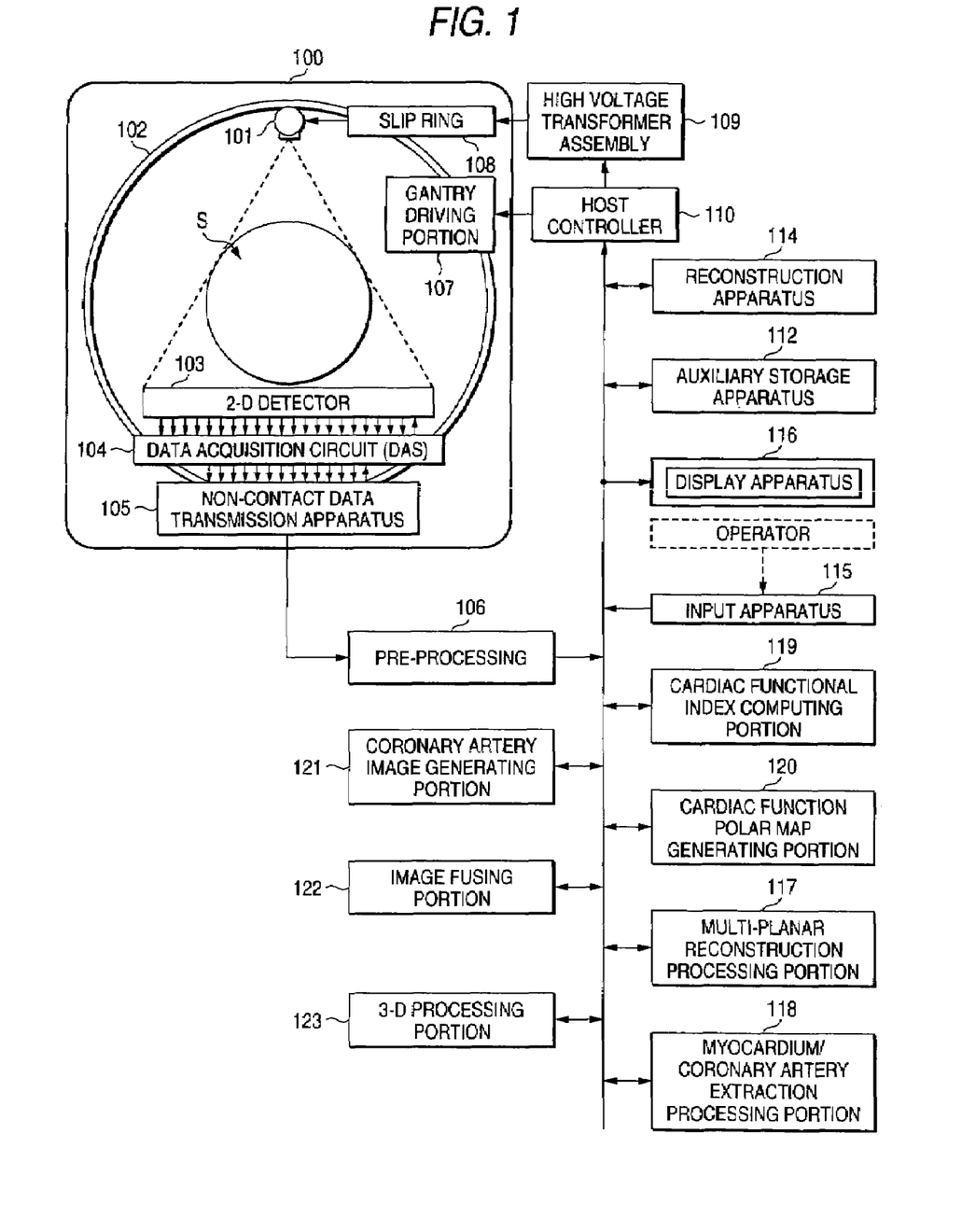
FIG. 1 is a schematic diagram of a computed tomographic apparatus according to a preferred embodiment of the invention.

FIG. 1 is a block diagram showing a configuration of a computed tomographic apparatus of this embodiment. A gantry portion 100 includes a rotational ring 102 that is rotated by a gantry driving portion 107. A cone-beam X-ray tube 101 and a multi-slice or 2-D array X-ray detector 103 are mounted to the rotational ring 102 to oppose each other having in between a cavity S into which a subject is inserted at the time of photographing. A high voltage generated successively or periodically in a high voltage transformer assembly 109 is applied to an X-ray tube 4 via a slip ring 108. An X-ray of a prismatic cone shape is thus irradiated.

In order to detect projection data of a plurality of slices simultaneously, the X-ray detector 103 comprises arrays of multi-channel detecting elements formed to shape an arc about a focal point (the vertex of the cone beam) of the X-ray tube 101 and aligned side-by-side along a direction parallel or nearly parallel to the rotational axis of the rotational ring 102, or a plurality of X-ray detecting elements aligned in a matrix manner in a planar or partially spherical shape with the center on the vertex of a cone beam.

A data acquisition circuit 104 generally referred to as a DAS (data acquisition system) is connected to the output of the X-ray detector 103. The data acquisition circuit 104 is provided with, for each channel, an I-V converter that converts a current signal in each channel of the X-ray detector 103 into a voltage, an integrator that integrates the resulting voltage signal periodically in sync with an X-ray exposure cycle, an amplifier that amplifies an output signal from the integrator, and an analog-to-digital converter that converts an output signal from the pre-amplifier to a digital signal. A pre-processing apparatus 106 receives an output (digital signal (referred to as pure data) from the data acquisition circuit 104 by means of light or magnetism via a non-contact data transmission apparatus 105 enabling non-contact data transmission, and performs pre-processing to the pure data, including correction of inhomogeneity in sensitivity among channels, compensation of significant deterioration in signal strength or missing of a signal due to a good X-ray absorbing substance, mainly, a metal portion, etc. Data outputted from the pre-processing apparatus 106 is referred to as raw data or projection data. The projection data is stored into an auxiliary storage apparatus 112, and is read out by a reconstruction apparatus 114 under the control of a host controller 110. The reconstruction apparatus 114 reconstructs image data related to a tomographic layer or a volume according to the Feldkamp method or any other reconstruction method based on a set of projection data from the auxiliary storage apparatus 112. The resulting image data is stored into the auxiliary storage apparatus 112 or displayed on a display apparatus 116 as a visible image.

Besides the basic components of an X-ray CT scanner, including the auxiliary storage apparatus 112, the reconstruction apparatus 114, the display apparatus 116, an input apparatus 115 having a keyboard, a pointing device or the like, the host controller 110 includes a multi-planar reconstruction processing portion 117, a myocardium/coronary artery extraction processing portion 118, a cardiac functional index computing portion 119, an initial polar map generating portion 120 that generates a polar map related to a cardiac function, a coronary artery image generating portion 121 that generates an image of a coronary artery structure developed on the polar coordinate system, a display image generating portion 122 that fuses the image of the coronary artery structure developed on the polar coordinate system into a polar map related to the cardiac function, and a 3-D processing portion 123 that realizes various kinds of 3-D processing including volume rendering, all of which are needed to form an image processing apparatus and realize an image processing method both being characteristics in this embodiment. These components will now be described in detail according to the processing procedure.

Figure 2:
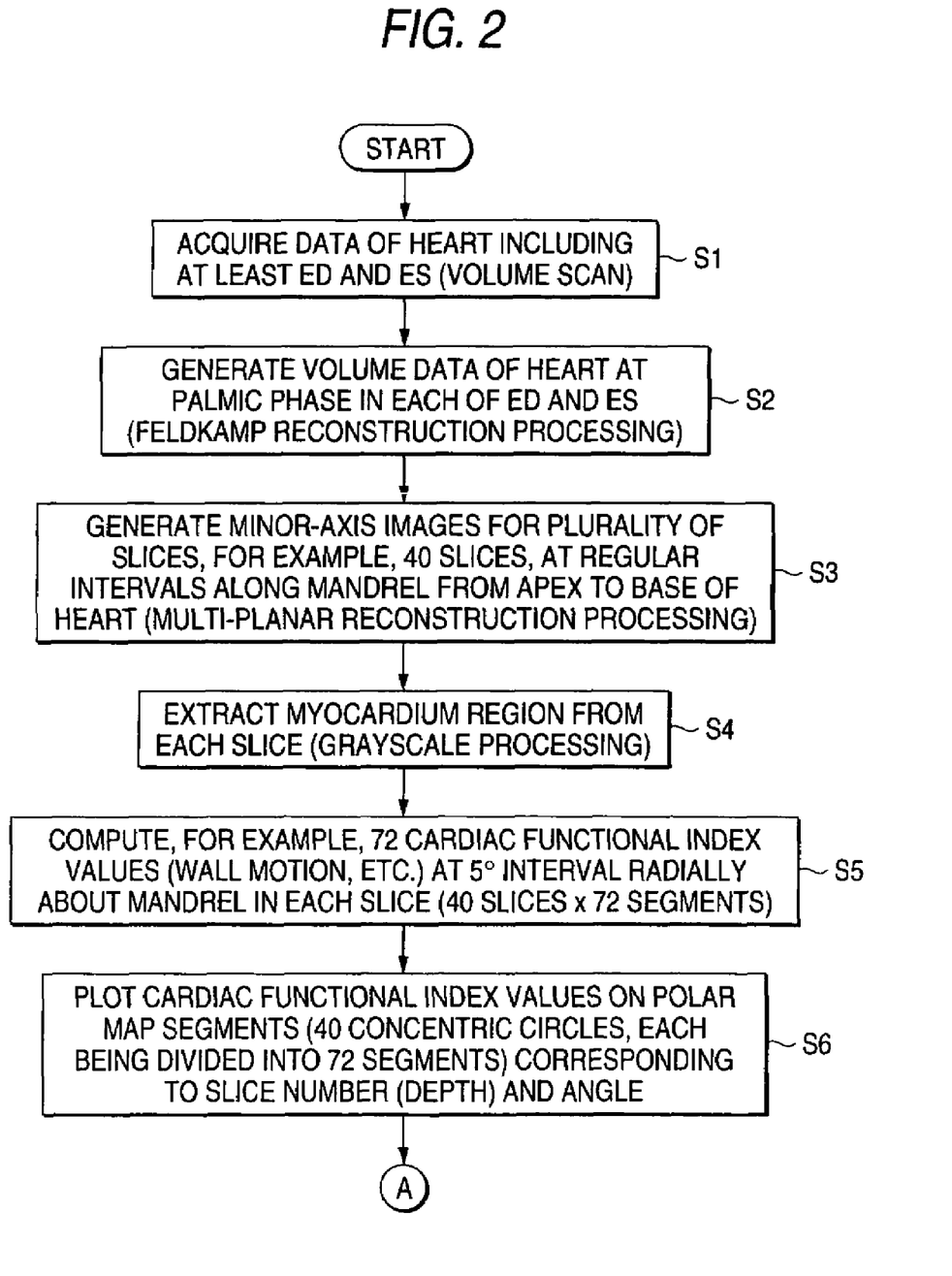
FIG. 2 is a flowchart showing a generation procedure of a polar map of cardiac functional indices in the embodiment.

FIG. 2 shows a generation procedure of a polar map of the cardiac function. Initially, after the intravenous injection of a contrast medium, a chest region of a subject including the heart is repetitively scanned at palmic phases including at least ED and ES (volume scan) (S1). Projection data at each palmic phase is thus acquired. Volume data corresponding to ED and volume data corresponding to ES are reconstructed based on the projection data thus acquired (S2).

Figure 4:
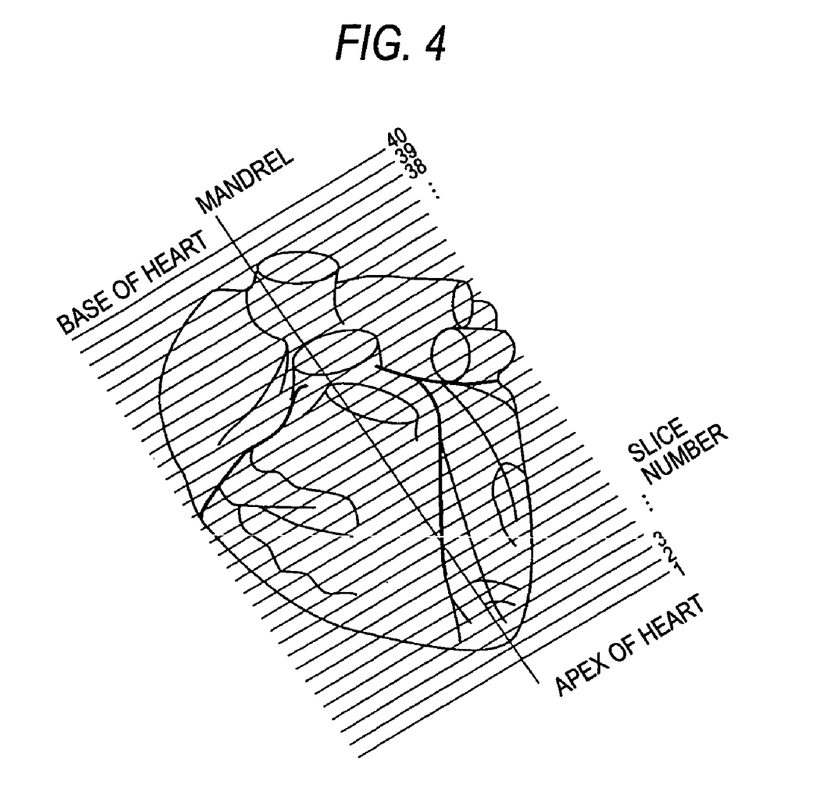
FIG. 4 is a supplemental view to multi-planar reconstruction processing in S3 of FIG. 2.

Then, as shown in FIG. 4, the multi-planar reconstruction processing portion 117 sets a plurality of slices intersecting at right angles with the myocardial axis of the left ventricle, which is recognized manually via the input apparatus 115 or automatically from the volume data in ED or ES, at regular intervals along the myocardial axis to correspond to a given number of slices (as many as concentric circles described below, herein, 40 slices) set via the input apparatus 115, and generates tomographic data (referred to as a minor-axis image) for each slice from the volume data in ED (S3). Likewise, the multi-planar reconstruction processing portion 117 generates, from the volume data in ES, tomographic data for each slice at the same position as the tomographic data in ED.

Figure 5:
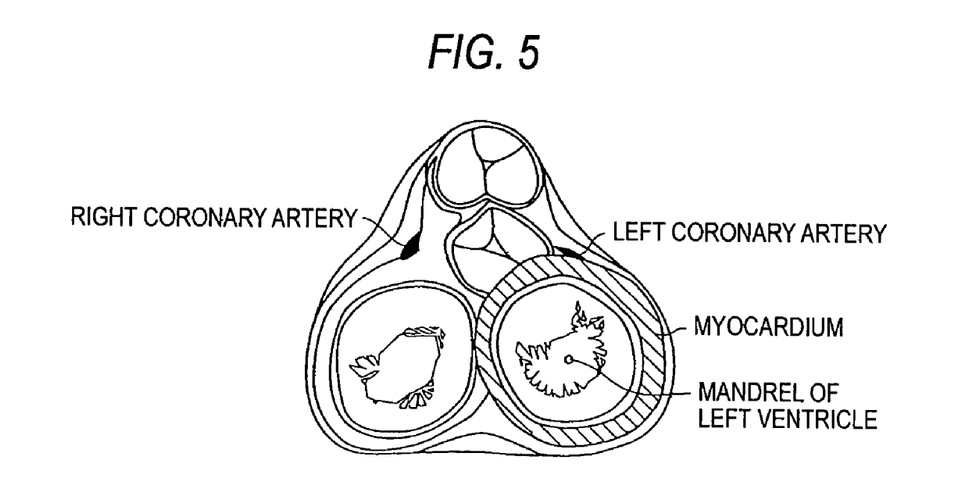
FIG. 5 is a view showing an example of a minor-axis image generated through multi-planar reconstruction processing in S3 of FIG. 2.

The myocardium/coronary artery extraction processing portion 118 extracts, as shown in FIG. 5, a myocardium region of the left ventricle from the tomographic data of each slice in ED through threshold processing (grayscale processing) or the like with respect to a CT number (S4). Likewise, the myocardium/coronary artery extraction processing portion 118 extracts a myocardium region of the left ventricle from the tomographic data of each slice in ES.

The contrast effect is exerted noticeably on a myocardium in the left ventricle at a specific time after the injection of a contrast medium. Hence, the threshold processing using the volume data acquired at this specific time makes it possible to extract the myocardium region in the left ventricle with high accuracy. In the above description, the tomographic data for each slice is generated first from the volume data (S3), and then the myocardium region in the left ventricle is extracted from each piece of tomographic data (S4); however, the myocardium region in the left ventricle may be extracted first from the volume data, and then each slice image may be generated from the extracted myocardium region in the left ventricle. In this case, the myocardial axis of the left ventricle may be specified more easily.

Figure 6:
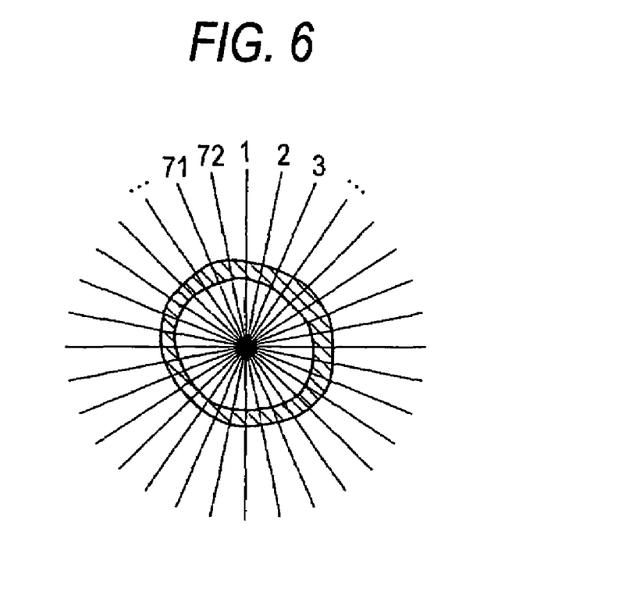
FIG. 6 is a supplemental view to cardiac functional index computation processing in S5 of FIG. 2.
Figure 7:
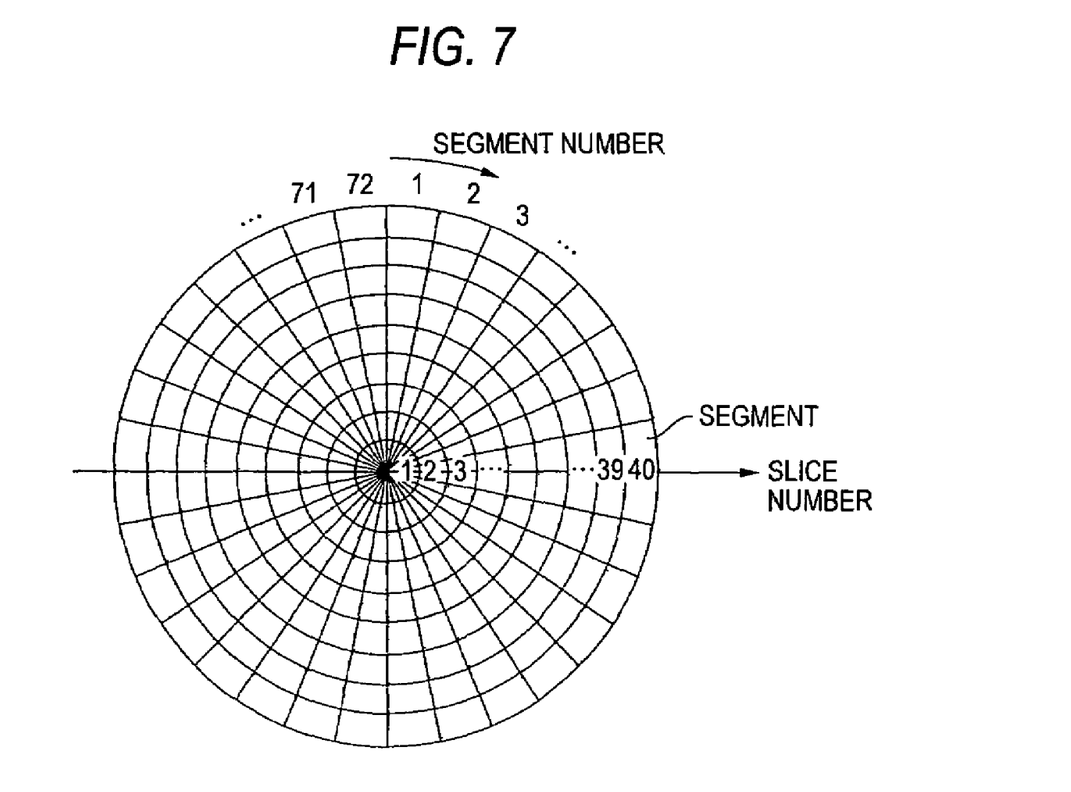
FIG. 7 is a supplemental view to cardiac functional indices plot processing in S6 of FIG. 2.

The cardiac functional index computing portion 119 computes, based on changes in the myocardium region in the same slices between the ED and ES, individual cardiac functional indices used to quantify the systolic function of the heart in a plurality of radial directions about the myocardial axis in the same number as segments of each concentric circle, herein 72 directions as shown in FIG. 6, which have been set via the input apparatus 115 (S5). The cardiac functional indices include, for example: wall motion obtained by subtracting a distance between the myocardial axis of the left ventricle and the outer wall of a myocardium in the left ventricle in ES from a distance between the myocardial axis of the left ventricle and the outer wall of a myocardium in the left ventricle in the ED; wall thickening obtained by subtracting the wall thickness of a myocardium in the left ventricle in the ED from the wall thickness of a myocardium in the left ventricle in ES, and then dividing (normalizing) the difference by the wall thickness of a myocardium in the left ventricle in ED; regional EF obtained by finding a volume change by subtracting a square of the inside diameter of a myocardium in the left ventricle in ES from a square of the inside diameter of a myocardium in the left ventricle in ED, and then dividing the volume change by a square of the inside diameter of a myocardium in the left ventricle in ES, etc. Indices of an arbitrary kind are chosen via the input apparatus 115.

The cardiac function polar map generating portion 120 develops the cardiac functional indices computed in the cardiac functional index computing portion 119 on the polar coordinate system, that is, generates polar map data related to the cardiac function by plotting the cardiac functional indices on a polar map template in the segment corresponding to the direction (segment number) within a concentric circle for a corresponding slice number (S6). According to the foregoing processing, the polar map data expressing the cardiac functional indices on the polar coordinate system can be generated.

Figure 3:
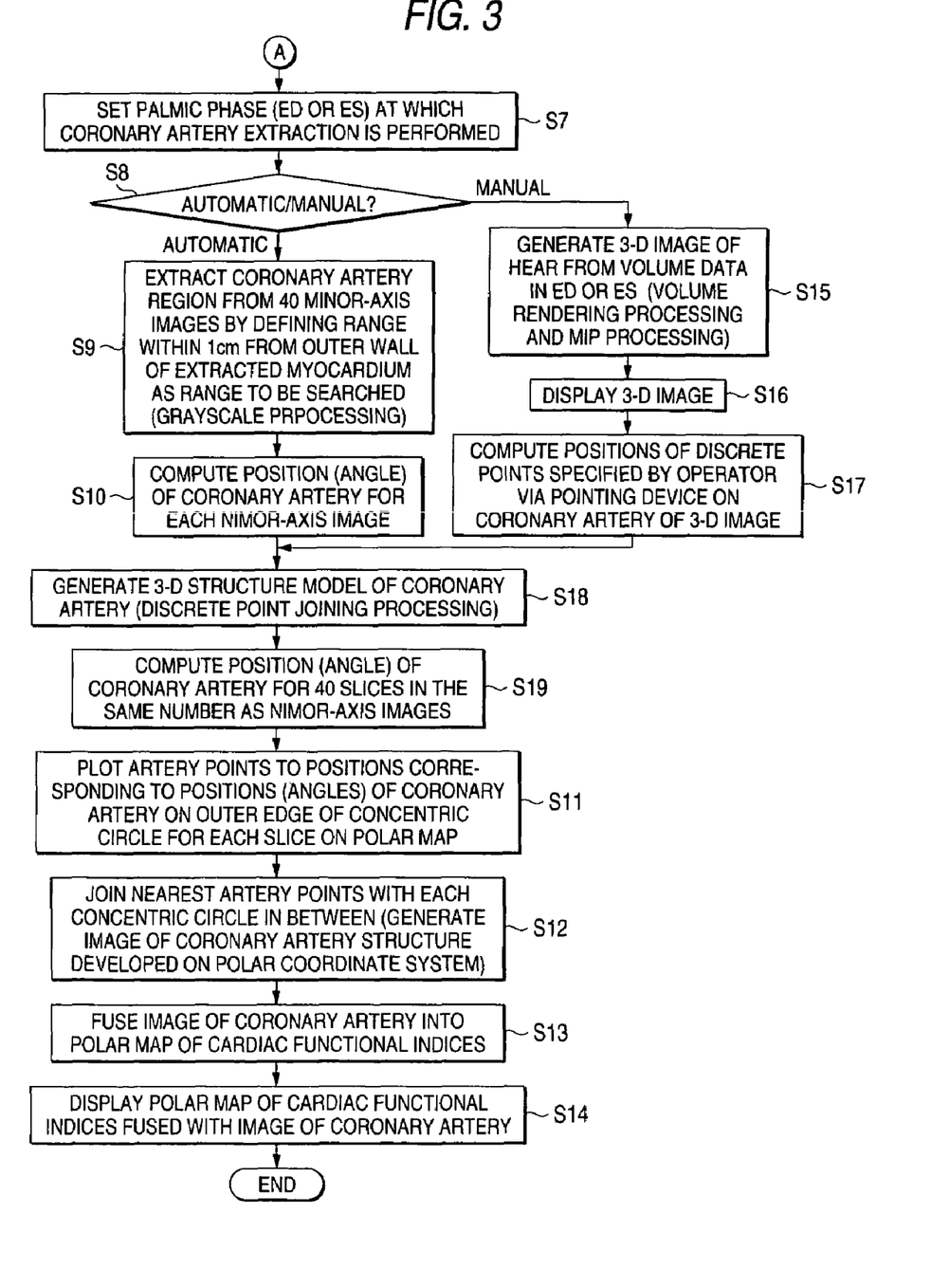
FIG. 3 is a flowchart showing a generation procedure of an image of a coronary artery structure developed on a polar coordinate system in the embodiment.

An explanation will now be given to generation of image data obtained by developing, on the polar coordinate system, the structure of an actual or approximate coronary artery related to the subject from whom the polar map data was generated. FIG. 3 shows the procedure. Initially, a particular palmic phase is set via the input apparatus 115 (S7). In this embodiment, automatic and manual (semi-automatic) methods are provided as a position calculating method of a coronary artery. The automatic method will be described first.

Figure 8:
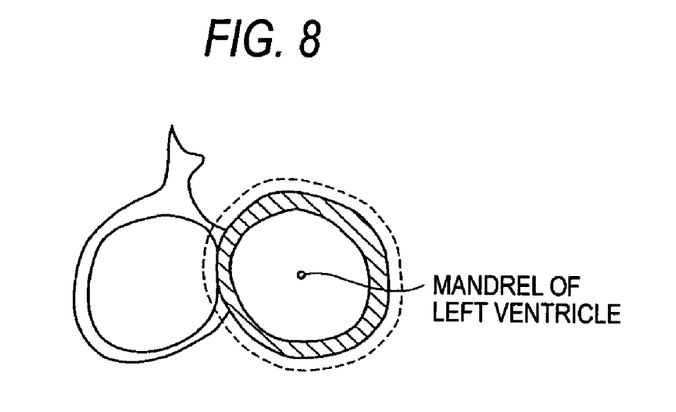
FIG. 8 is a supplemental view to coronary artery region extraction processing in S9 of FIG. 3.

Initially, the tomographic data set of 40 slices having been generated in S3 and corresponding to the palmic phase set in S7 is supplied to the myocardium/coronary artery extraction processing portion 118. As shown in FIG. 8, the myocardium/coronary artery extraction processing portion 118 extracts a coronary artery region from the tomographic data of each slice by defining a range, for example, 1 cm outside from the myocardium region extracted in S4 as a range to be searched (S9).

Figure 9:
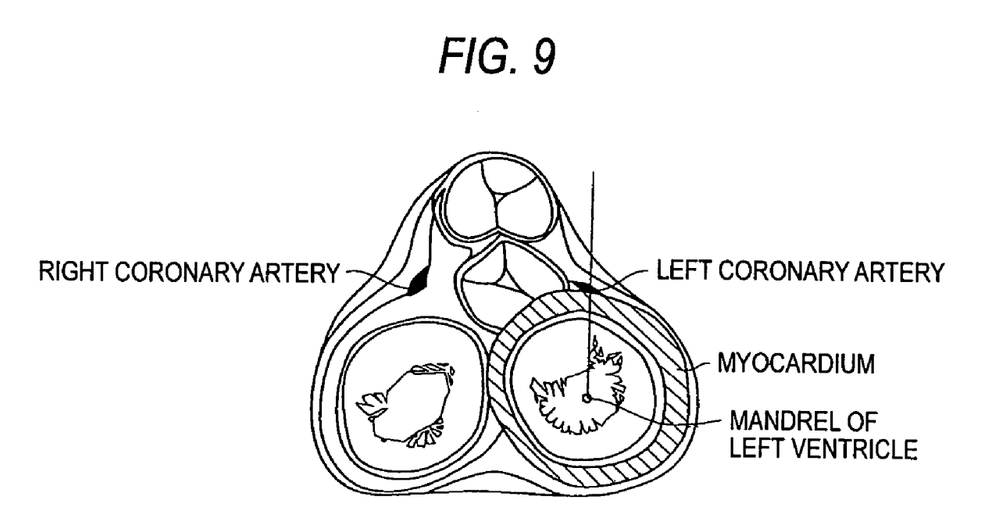
FIG. 9 is a supplemental view to coronary artery region position computation processing in S10 of FIG. 3.
Figure 15:
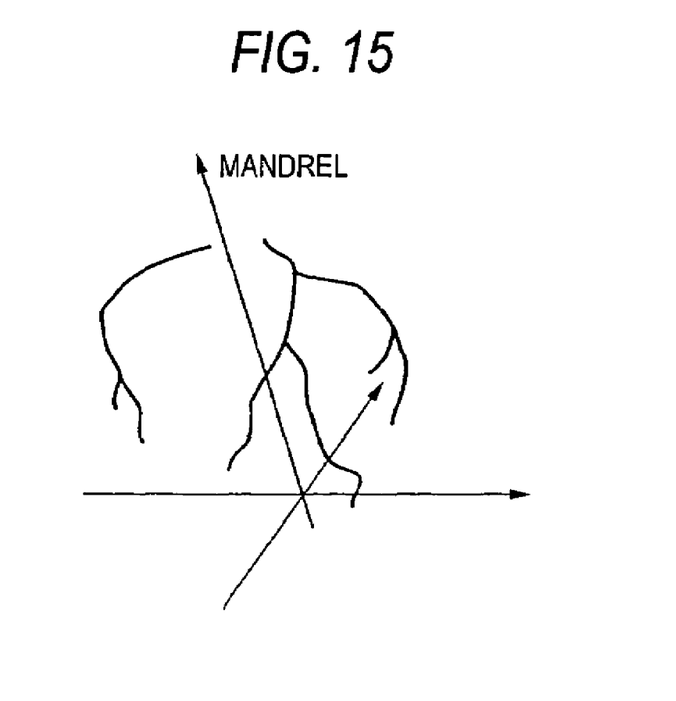
FIG. 15 is a supplemental view to generation processing of an image of the coronary artery structure developed on the polar coordinate system in S18 of FIG. 3.
Figure 16:
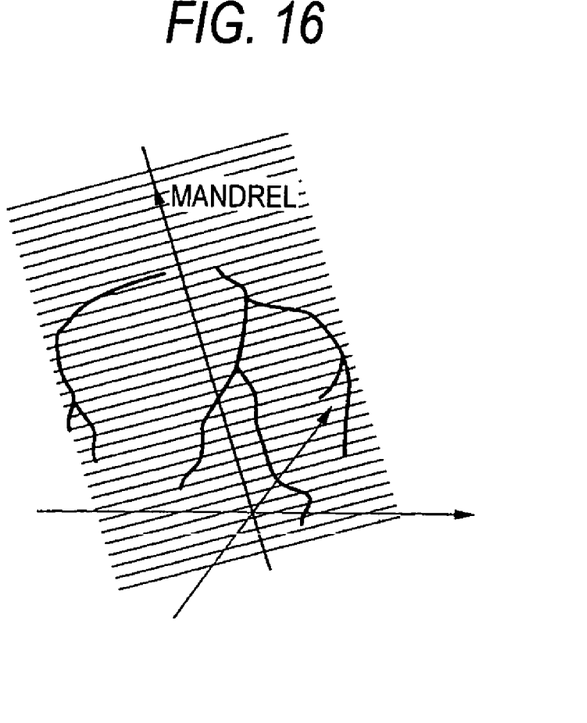
FIG. 16 is a supplemental view to coronary artery position computation processing in S19 of FIG. 3.

Then, as shown in FIG. 9, the image generating portion 121 computes a position of the extracted coronary artery region (herein, the angle about the myocardial axis) for each slice (S10). Subsequently, the 3-D processing portion 123 generates a 3-D structure model of the coronary artery as shown in FIG. 15, by joining the nearest discrete points thus computed with a straight line in a direction from the apex to the base of the heart and also in an opposite direction (S18). The image generating portion 121 sets, as shown in FIG. 16, slices in the same number (40) and at the same intervals as the minor-axis images in the 3-D structure model of the coronary artery thus generated, and computes the position (angle about the myocardial axis) of the coronary artery region in each slice (S19).

Figure 10:
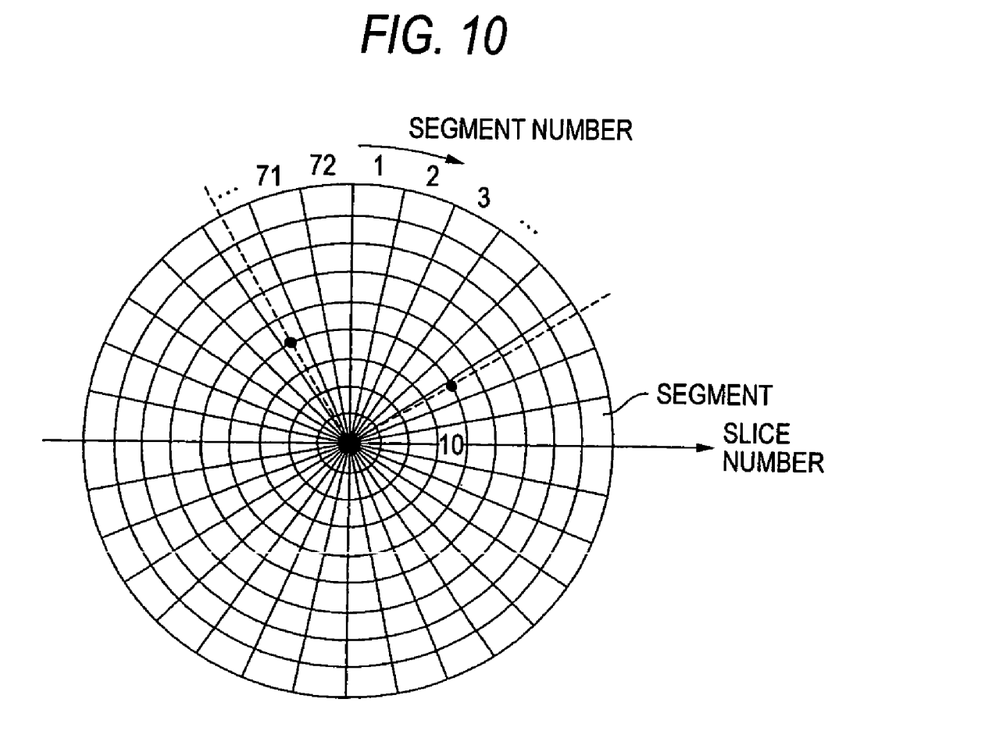
FIG. 10 is a first supplemental view to artery point plot processing in S11 of FIG. 3.
Figure 11:
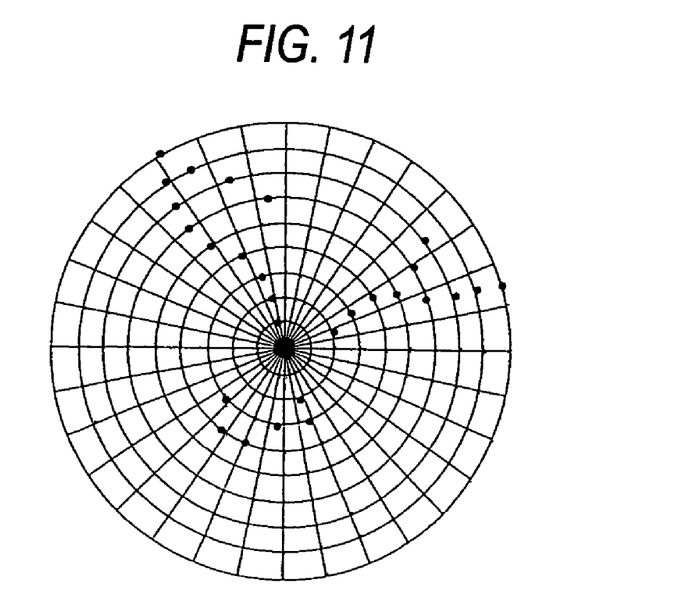
FIG. 11 is a second supplemental view to the artery point plot processing in S11 of FIG. 3.

Further, as shown in FIG. 10, the image generating portion 121 plots a point (referred to as the artery point) to the position corresponding to the computed angle on the outer edge of the concentric circle for the slice number on the polar map template of the same style as the polar map (S1). FIG. 11 shows a polar map template when the artery points for all the slices have been plotted.

Figure 12:
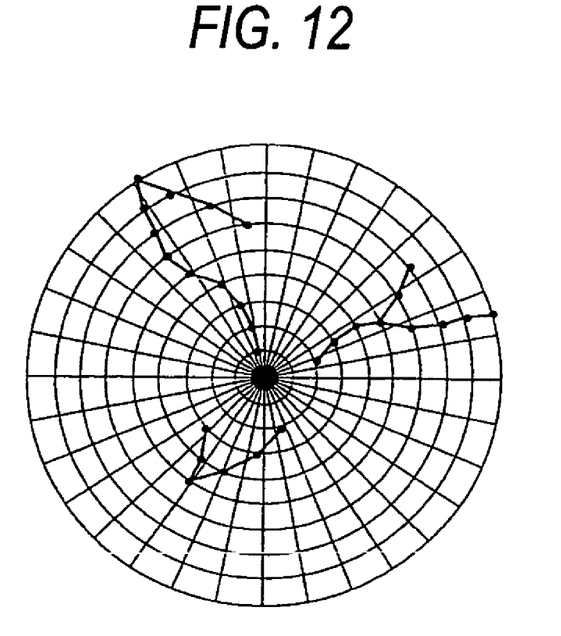
FIG. 12 is a supplemental view to artery point joining processing in S12 of FIG. 3.

The image generating portion 121 joins, as shown in FIG. 12, the nearest artery points using a straight line with each concentric circle in between from the center of the circle (the apex of the heart) to the outside (the base of the heart), and further joins the nearest artery points using a straight line with each concentric circle in between in an opposite direction from the outside (the base of the heart) to the center of the circle (the apex of the heart), thereby generating an image of the coronary artery structure developed on the polar coordinate system (S12). By joining the artery points in the both directions as has been described, it is possible to address the branching of a coronary artery. The joining processing is preferably performed automatically or manually with the use of anatomical knowledge of a coronary artery.

Figure 13:
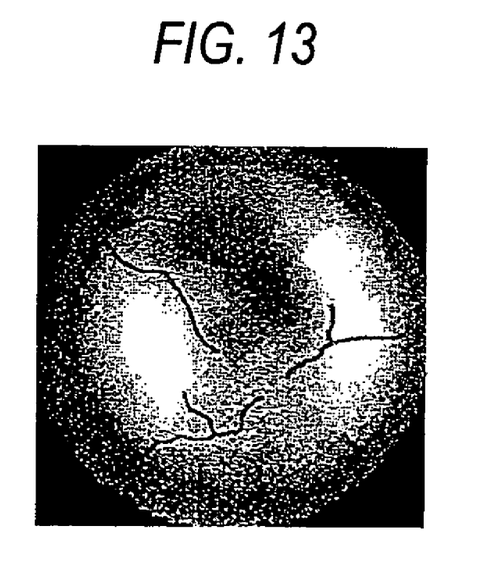
FIG. 13 shows a grayscale image as an example of actual display of a polar map fused with an image of the coronary artery structure developed on the polar coordinate system in the embodiment.

The image fusing portion 122 fuses the image of the coronary artery structure developed on the polar coordinate system into the polar map of the cardiac functional indices generated in S6 (S13). A polar map of the cardiac functional indices fused with the image of the coronary artery structure developed on the polar coordinate system is then displayed as shown in FIG. 13 (S14).

Figure 14:
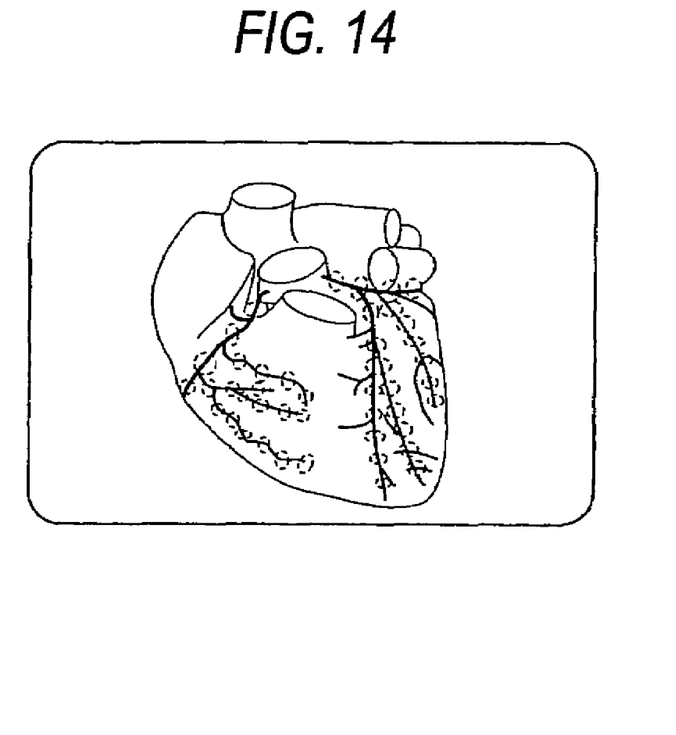
FIG. 14 is a supplemental view to coronary artery specifying processing in S17 of FIG. 3.

The manual method will now be described with reference to FIG. 3 again. Initially, in S15, the 3-D processing portion 123 generates a 3-D image of the heart as shown in FIG. 14 through volume rendering processing and MIP processing (maximum intensity projection processing) from the volume data in ED or ES or the tomographic data (minor-axis image data) of 40 slices generated in S3. The 3-D image of the heart is then displayed on the screen of the display apparatus 116 as shown in FIG. 14 (S16). The operator specifies a plurality of points discretely on the image of the coronary artery displayed on the 3-D image as indicated by a dotted line of FIG. 14 with the use of the pointing device of the input apparatus 115. The positions of the discrete points are computed in the 3-D processing portion 123 (S17). Then, the 3-D processing portion 123 joins the nearest discrete points thus computed in a direction from the apex to the base of the heart and also in an opposite direction, thereby generating a 3-D structure model of the coronary artery as shown in FIG. 15 (S18).

The image generating portion 121 sets, as shown in FIG. 16, slices in the same number (40) and at the same intervals as the minor-axis images in the 3-D structure model of the coronary artery thus generated, and computes the position (angle about the myocardial axis) of the coronary artery region in each slice (S19). Subsequent S11 through S14 are same as described above.

As has been described, by displaying a polar map of the cardiac functional indices superimposed with an image of the structure of a coronary artery related to an actual subject, which is developed on the polar coordinate system, the observer becomes able to distinguish a dominant region of a coronary artery having a lesion; moreover, he becomes able to specify or estimate a specific position of the lesion in the coronary artery.

Figure 17:
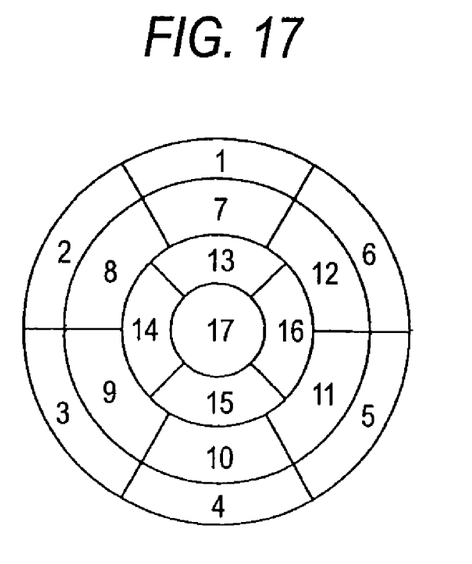
FIG. 17 is a view showing an example of a template for re-segmentation in the embodiment.

It should be noted that the polar map generating portion 120 is furnished with a function of re-distributing the polar map generated from 40 concentric circles×72 (segments (referred to as basic segments) to anatomically meaningful segmentation as shown in FIG. 17. Each segment shown in FIG. 17 includes a plurality of basic segments, and the average value, the maximum value, and minimum value, and the maximum frequency value of the cardiac functional index values of the plurality of basic segments included in each segment are computed, and allocated to each segment as characteristic values. This makes it possible to re-generate a polar map having various meanings in terms of clinical diagnosis. Being the same polar coordinate expression, it goes without saying that an image of the coronary artery structure developed on the polar coordinate system can be fused into the re-generated polar map.

Figure 18A:
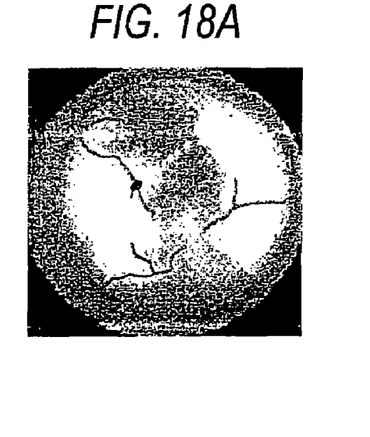
FIG. 18A to FIG. 18E are views showing curved MPR images corresponding to a specified point in the embodiment.
Figure 18B:
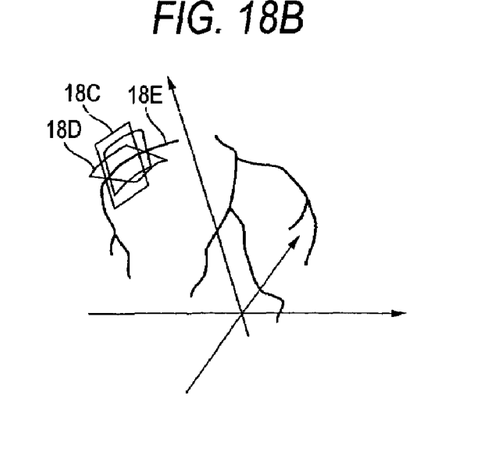

Also, the 3-D processing portion 123 is furnished with a function of generating a curved MPR image (see FIGS. 18B, 18D, and 18E) corresponding to an arbitrary point on the image of a coronary artery specified via the input apparatus 115, as shown in FIG. 18A, on the image of the coronary artery structure developed on the polar coordinate system or on the polar map. The curved MPR image of FIG. 18D is a morphological tomographic image related to a curved plane defined as a line of a certain length intersecting at right angles with the myocardial axis moves along the coronary artery including the specified point, and is reconstructed from the volume data related to an arbitrary palmic phase. The curved MPR image of FIG. 18E is a morphological tomographic image related to a curved plane defined as a line of a certain length parallel to the myocardial axis moves along the coronary artery including the specified point, and is reconstructed from the volume data related to an arbitrary palmic phase. This curved MPR image enables observation of an image of a major-axis image along an artery of the heart including a myocardium. For example, by specifying a point suspected as having a lesion, a tissue structure of a peripheral myocardium or the like can be observed longitudinally, which in turn makes it possible to specify a lesion-causing point.

Figure 18C:
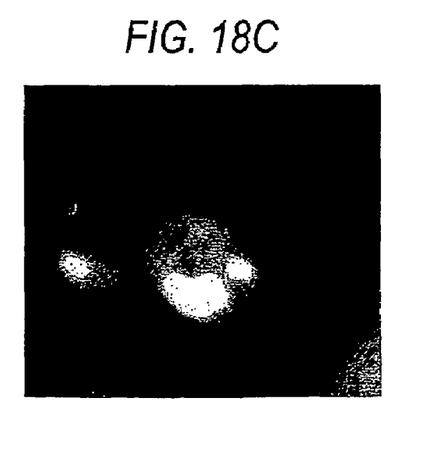
Figure 18D:
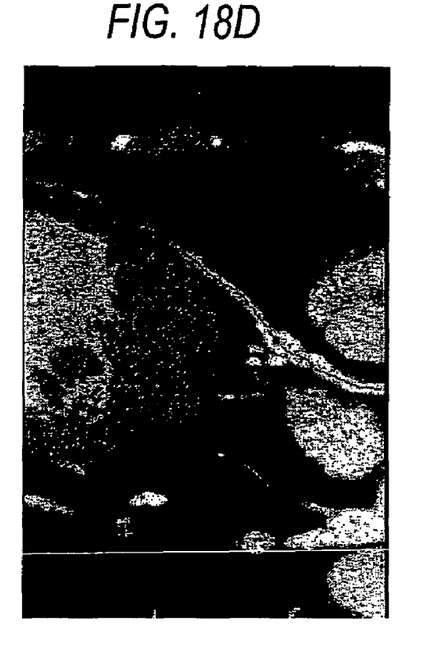
Figure 18E:
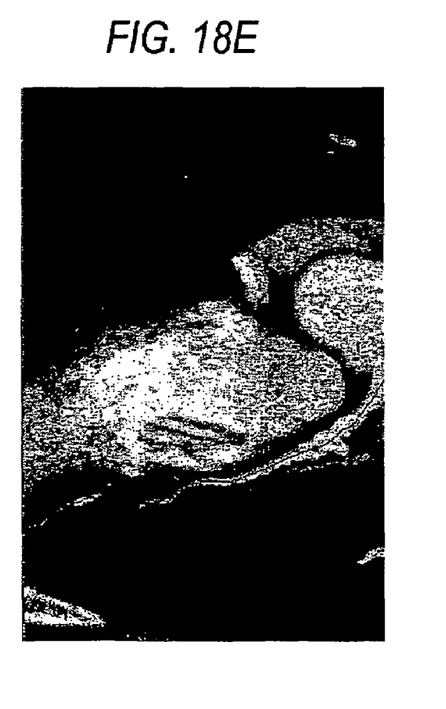
Figure 19A:
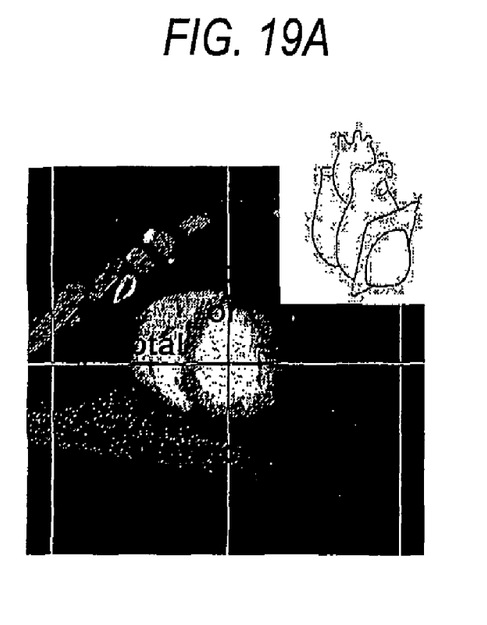
FIG. 19A to FIG. 19C are views showing MPR images corresponding to a specified point in the embodiment.
Figure 19B:
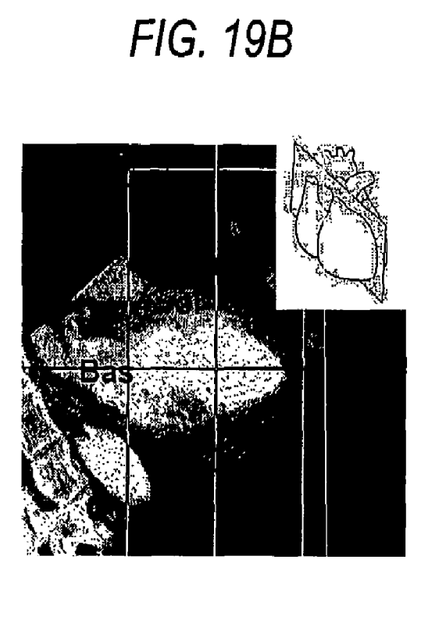
Figure 19C:
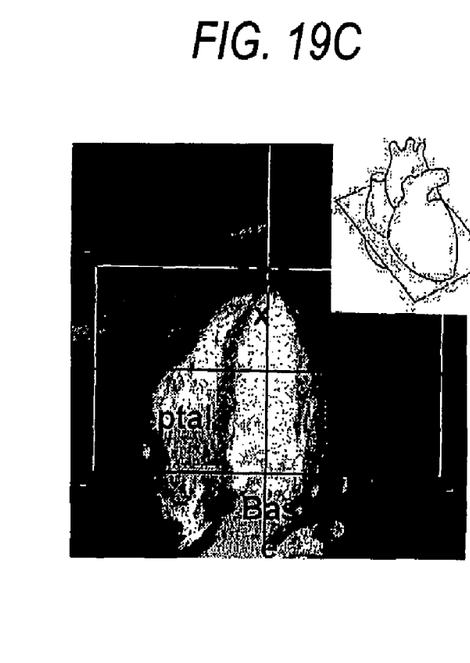

The 3-D processing portion 123 is also furnished with a function of generating an MPR image as shown in FIG. 18C, corresponding to a plane passing an arbitrary point on the image of a coronary artery specified on the polar map via the input apparatus 115 and intersecting at right angles with an axis of an artery. Further, the 3-D processing portion 123 is furnished with a function of generating a minor-axis image intersecting at right angles with the myocardial axis as shown in FIG. 19A. Furthermore, the 3-D processing portion 123 is furnished with a function of generating an image of a plane parallel to the myocardial axis as shown in FIGS. 19B and 19C.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An image processing apparatus, comprising:
an index computing unit configured to compute motion functional indices of a particular organ from volume data of a subject including said particular organ;
a polar map generating unit configured to generate a polar map by developing said indices on a polar coordinate system;
an image generating unit configured to generate, from said volume data, an image related to a structure of one of said particular organ and a peripheral organ developed on the polar coordinate system;
a fusing unit configured to fuse said image into said polar map; and
a display unit configured to display said polar map fused with said image.

2. The image processing apparatus according to claim 1, wherein said particular organ is a heart, said motion function is a contraction rate of a myocardium, and said peripheral organ is a coronary artery.

3. The image processing apparatus according to claim 2, wherein said polar coordinate system is expressed by an angle about a myocardial axis of the heart, and a distance from one of an apex and a base of the heart.

4. The image processing apparatus according to claim 2, wherein said coronary artery is searched through a range within a certain distance from an outer wall of the myocardium.

5. The image processing apparatus according to claim 1, further comprising an image generating unit that generates, from said volume data, an image related to a plane passing an arbitrary point on said image being displayed.

6. The image processing apparatus according to claim 2, further comprising an image generating unit that generates, from said volume data, an image related to a plane passing an arbitrary point on said image of the coronary artery.

7. The image processing apparatus according to claim 6, wherein said plane is parallel to said myocardial axis of the heart.

8. The image processing apparatus according to claim 6, wherein said plane is perpendicular to said myocardial axis of the heart.

9. The image processing apparatus according to claim 6, wherein said plane is curved along said coronary artery.

10. An image processing method, comprising:
computing motion functional indices of a particular organ from volume data of a subject including said particular organ;
generating a polar map by developing said indices on a polar coordinate system;
generating, from said volume data, an image related to a structure of one of said particular organ and a peripheral organ developed on the polar coordinate system;
fusing said image into said polar map; and
displaying said polar map fused with said image.

11. The image processing method according to claim 10, wherein said particular organ is a heart, said motion function is a contraction rate of a myocardium, and said peripheral organ is a coronary artery.

12. The image processing method according to claim 11, wherein said polar coordinate system is expressed by an angle about a myocardial axis of the heart, and a distance from one of an apex and a base of the heart.

13. The image processing method according to claim 11, wherein said coronary artery is searched through a range within a certain distance from an outer wall of the myocardium.

14. The image processing method according to claim 10, further comprising generating, from said volume data, an image related to a plane passing an arbitrary point on said image being displayed.

15. The image processing method according to claim 11, further comprising generating, from said volume data, an image related to a plane passing an arbitrary point on said image of the coronary artery.

16. The image processing method according to claim 15, wherein said plane is parallel to said myocardial axis of the heart.

17. The image processing method according to claim 15, wherein said plane is perpendicular to said myocardial axis of the heart.

18. The image processing method according to claim 15, wherein said plane is curved along said coronary artery.

19. An X-ray computed tomographic apparatus, comprising:
a data acquiring unit configured to acquire projection data of a subject;
a reconstructing unit configured to reconstruct one of multi-slice data and volume data based on said projection data;
an index computing unit configured to compute motion functional indices of a particular organ from one of said multi-slice data and said volume data;
a polar map generating unit configured to generate a polar map by developing said indices on a polar coordinate system; and
a display unit configured to display said polar map.

20. The X-ray computed tomographic apparatus according to claim 19, wherein said reconstructing unit reconstructs an X-ray CT image.

* * * * *